(12) United States Patent
Osawa et al.

(10) Patent No.: US 6,187,264 B1
(45) Date of Patent: Feb. 13, 2001

(54) SOLUTION FOR PRESERVING AND STERILIZING CONTACT LENSES

(75) Inventors: Nobuyuki Osawa; Seiichiro Ikawa, both of Tokyo (JP)

(73) Assignee: Asahi Kasei Kogyo Kabushiki Kaisha, Osaka (JP)

( * ) Notice: Under 35 U.S.C. 154(b), the term of this patent shall be extended for 0 days.

(21) Appl. No.: 09/117,625

(22) PCT Filed: Jan. 29, 1997

(86) PCT No.: PCT/JP97/00198

§ 371 Date: Aug. 26, 1998

§ 102(e) Date: Aug. 26, 1998

(87) PCT Pub. No.: WO97/27879

PCT Pub. Date: Aug. 7, 1997

(30) Foreign Application Priority Data

Feb. 2, 1996 (JP) .................................. 8-17418

(51) Int. Cl.[7] .................................................. A61L 12/08
(52) U.S. Cl. .............................. 422/28; 514/839; 514/840
(58) Field of Search ............................... 422/28; 514/839, 514/840, 12, 13; 424/405

(56) References Cited

FOREIGN PATENT DOCUMENTS 5-310544  * 11/1993  (JP) .
7-170957  *  7/1995  (JP) .
9-10288   *  1/1997  (JP) .
94/13774  *  6/1994  (WO) .

* cited by examiner

Primary Examiner—William H. Beisner
(74) Attorney, Agent, or Firm—Young & Thompson

(57) ABSTRACT

A solution for preserving and/or disinfecting a contact lens characterized by containing polylysine.

11 Claims, No Drawings

SOLUTION FOR PRESERVING AND STERILIZING CONTACT LENSES

TECHNICAL FIELD

This invention relates to a solution for preserving and/or disinfecting contact lenses.

BACKGROUND ART

Contact lenses are generally classified as hard contact lenses and water-containing soft contact lenses. Both types must be kept in their respective preserving solutions while they are not being worn, in order to preserve their delicate shape and performance. In particular, water-containing soft contact lenses should be stored in physiological saline to keep a constant water content thereby maintaining the characteristic softness that assures comfort in use.

Preserving solutions for contact lenses usually contain preservatives in concentrations of several parts per million to several percent, for the purpose of suppressing growth of bacteria and the like that enters through the opening of a container.

The preservatives must be harmless to the mucous membranes of the eyes and, at the same time, should not adversely affect the lenses. Benzalkonium chloride and chlorobutanol are effective antimicrobial agents currently and widely employed as such a preservative. They are used, of necessity, at concentrations safe to the eye mucosa. However, these preservatives are not suitable for certain water-containing soft contact lenses or hard contact lenses that have a high silicone content.

That is, in certain circumstances, the above-described preservatives penetrate into the inside of a lens and gradually concentrate in the inside. In the case of a water-containing soft contact lens, the inside concentration eventually reaches a level that might cause irritation to the eye mucosa. In the case of a high-silicone hard contact lens, the inside concentration is also problematical. Above all, the hydrophilic properties of the lens are reduced, which seriously impairs the comfort while the lens is being worn.

Water-containing soft contact lenses should be disinfected after use and before storage, to remove bacteria attached thereto while in use. Disinfection is usually effected by boiling. The microbicidal effect of hydrogen peroxide is also useful for disinfection.

However, in order to disinfect lenses by boiling, it is necessary for a user to procure a dedicated boiler and to secure a power source for operating the boiler, which is very inconvenient for a user especially when travelling.

This problem is avoided by using hydrogen peroxide instead of a boiler, but in this case a user must prepare two liquids, a preserving solution and a disinfectant, wherever he or she is (in places where such liquids are not available, a user must always bring the liquids with him or her). Further, disinfection with hydrogen peroxide should be followed by careful and certain neutralization of hydrogen peroxide remaining on the lenses.

Whichever disinfection technique is chosen, it has been an economical burden and an inconvenience for soft contact lens users to carry out storage and disinfection in separate systems.

In order to overcome these problems a solution for contact lenses with which disinfection and preservation (storage) can be effected simultaneously has recently been proposed, as an aqueous solution containing a polymer of a biguanide compound (see JP-A-61-85301 (the term "JP-A" as used herein means an "unexamined published Japanese patent application")) and as an aqueous solution containing a polymer of poly(ammonium chloride) (see JP-W-A-83-501515 (the term "JP-W-A" as used herein means an "published Japanese national stage of international application")).

However, biguanide compounds tend to decompose during long-term storage. Unless used up in a short time after the preparation, the solution will reduce its crystalloid, which raises the concern that not only the disinfecting ability but also the storage stability of the solution is reduced.

Further, poly(ammonium chloride) does not have sufficient heat resistance. Since water-containing soft contact lenses must be sterile when shipped from a manufacturing factory, containers containing lenses are usually sterilized by autoclaving at a temperature of 120° C. Poly(ammonium chloride) has a possibility of being decomposed by the high temperature. Eventually, two solutions, one for use in the sterilization and one for usual handling, should be prepared separately. Thus, a single solution is incapable of handling a contact lens from the shipment through the use.

An object of the present invention is to solve the above-described problems of conventional techniques and to provide a liquid for easy preservation and/or disinfection of a contact lens, which is applicable to any type of contact lenses and capable of preserving and disinfecting a contact lens, and which needs no special care after a disinfection.

DISCLOSURE OF THE INVENTION

The inventors have conducted extensive investigations in order to accomplish the above object. As a result, they have found that polylysine not only imparts storage stability to a solution for contact lenses containing the same, but also is effective in disinfecting contact lenses from bacteria that adheres thereto in use; on that basis, the present invention has been made.

The present invention relates to a solution for preserving a contact lens which is characterized by containing polylysine; a solution for disinfecting a contact lens which is characterized by containing polylysine; a solution for preserving and disinfecting a contact lens which is characterized by containing polylysine; and a method for preserving and/or disinfecting a contact lens which is characterized by using a solution containing polylysine.

THE BEST MODES FOR CARRYING OUT THE INVENTION

Polylysine is a polymer of L-lysine, usually composed of 20 to 50 lysine residues. It is obtainable through, for example, generally employed organic synthesis from L-lysine (see *Journal of the American Chemical Society*, Vol. 78, p. 764).

Polylysine can also be produced on an industrial scale by culturing a microorganism belonging to the genus Streptomyces according to applied biotechnology (see JP-B-59-20359, the term "JP-B" as used herein means an "examined Japanese patent publication").

In addition, polylysine preparations are commercially available from Chisso Corp., which contain various adjuvants for potentiating polylysine.

Polylysine which can be used in the present invention includes α-polylysine resulting from condensation between an α-positioned amino group and a carboxyl group and ε-polylysine resulting from condensation between an ε-positioned amino group and a carboxyl group. The ε-polylysine is preferred.

The antimicrobial effect of polylysine is expressed in terms of minimum inhibitory concentration (MIC) against various bacteria. Polylysine inhibits the growth of bacteria, such as *Escherichia coli, Pseudomonas aeruginosa*, and *Staphylococcus aureaus*, at 100 ppm or lower, and the growth of black mold and yeasts at 300 ppm or lower.

Polylysine is approved as a food additive and in fact used as a preservative in many foods, such as fast food, deli food, convenience store food, etc. However, use of polylysine is currently confined to a food additive while its broad antimicrobial spectrum and safety to living bodies have been confirmed.

Because polylysine is, while solid per se, strongly deliquescent, it is usually used in the form of a very thick aqueous solution. Therefore, it dissolves in water in any concentration, and, for use as a solution for preservation and disinfection of contact lenses, the concentration of the solution can be adjusted arbitrarily.

The polylysine concentration of the solution used for preservation and/or disinfection of contact lenses preferably ranges from 1 ppm to 10%, while varying depending on the kind of microorganisms to be controlled. A more preferred concentration range is from 10 ppm up to 1%.

A particularly preferred concentration for lens preservation is from 10 to 1000 ppm, and for disinfection from 100 ppm to 1%.

In concentrations lower than 1 ppm, the antimicrobial effect is insufficient against some microorganisms. If the concentration exceeds 10%, no improvement-in effect is produced, while the cost is higher.

It has turned out that polylysine, the solute of the solution according to the present invention, being a high-molecular weight compound having a chemical structure composed of polymerized lysine residues, has little or no penetrability into the inside of a lens. That is, the present invention provides the best countermeasure against a low-molecular preservative's penetration into the inside of a lens as mentioned in the "Background Art" section.

While sufficient effects are expected of the solution for contact lens preservation and/or disinfection containing polylysine alone, the solution can contain other additives for enhancing the inhibitory effect on the growth of bacteria and the like and the disinfectant effect.

Such additives that can enhance the antimicrobial effect of polylysine include ethyl alcohol, glycine, and acetic acid. An appropriate choice is made among them according to the kind of the microorganism to be controlled and the purpose of use.

The additives enumerated above exhibit antimicrobial effect of themselves and are expected to produce a synergistic effect with polylysine. Addition of other antimicrobial substances is conceivable, but anionic substances such as soap and carboxylic acids cannot be used in combination with polylysine because they form white turbid matter with polylysine and settle in the solution.

It is preferable to add to the solution for contact lens preservation and/or disinfection an appropriate component for making it substantially isotonic (hereinafter referred to as an isotonic component) at a concentration of from 0.1 to 3.0% by weight, more preferably from 0.5 to 2.0% by weight. Lavish use of sodium chloride, in particular, should be avoided because it tends to lessen the antimicrobial effect of polylysine if added in concentrations exceeding 3.0%.

Examples of useful isotonic components include inorganic acid salts, such as sodium chloride, potassium chloride, and magnesium chloride; acids, such as hydrochloric acid, acetic acid, and citric acid; and alkalis, such as sodium hydroxide and sodium citrate. Substances generally known as a buffer, such as boric acid, borax, sodium phosphate, and sodium phosphite, can also be used as an isotonic component either alone or in combination.

In particular, boric acid is capable of pH adjustment, and its aqueous solution is useful as a disinfectant that can be used with safety as is seen from its current application to disinfection in the treatment of eye diseases and throat diseases. Accordingly, it is also expected to have a disinfectant effect when added to the aqueous solution for contact lenses according to the present invention.

The pH of the solution according to the present invention is preferably adjusted in the vicinity of neutrality, e.g., in a range of 6 to 8, particularly 6.5 to 7.5. From this viewpoint, too, buffers can be used as an isotonic component. Inorganic or organic acids, such as hydrochloric acid, citric acid and acetic acid, and/or their salts, and inorganic or organic alkalis, such as sodium hydroxide and sodium citrate, can also be used for the pH adjustment.

For the purpose of removing accumulated dirt mainly comprising tear-derived calcium from the lens after use, the solution of the present invention preferably contains a chelating agent, such as disodium ethylenediaminetetraacetate (hereinafter abbreviated as EDTA-2Na) and sodium hexametaphosphate, at a concentration of from 0.001 to 1.0% by weight, more preferably from 0.01 to 0.5% by weight. Besides being effective in cleaning a lens, the chelating agent exhibits antimicrobial properties because of its chelating effect. Therefore, use of the chelating agent contributes to achieving the object of the present invention.

To increase the availability of polylysine when preparing a preserving and/or disinfecting solution for contact lenses, the present invention includes within its scope the supply of polylysine preparations in the form of various tablets including effervescent water-soluble tablets and non-effervescent water-soluble tablets, powders, and granules.

Polylysine as obtained in the form of a thick aqueous solution can be formulated into various tablets, powders or granules together with the above-mentioned salts, acids, etc. for obtaining isotonic properties, such as sodium chloride, potassium chloride, magnesium chloride, hydrochloric acid, citric acid, sodium citrate, boric acid, borax, and sodium primary phosphate. These polylysine preparations can also be prepared by using appropriate inert ingredients customarily used in the preparation of water-soluble tablets, powders and granules, such as carriers, lubricants, crystal agents or vehicles, e.g., polyethylene glycol, dextran, lactose, crystalline cellulose, etc.

Where polylysine is formulated together with an effervescent salt, such as a mixture of citric acid or tartaric acid and sodium hydrogencarbonate, effervescent tablets, powders or granules are obtained, with which a solution for contact lens preservation and/or disinfection can be prepared with great ease.

The tablets, powders or granules of polylysine prepared with suitable commonly used carriers, lubricants, vehicles, etc. appropriately combined with the acids or salts for obtaining isotonic properties are dissolved in purified water, etc. to provide a preserving and/or disinfecting solution suited to contact lenses.

Another method for preparing a solution for contact lens preservation and/or disinfection when necessary comprises adding several drops of a thick, e.g., 20 to 50 wt %, aqueous solution of polylysine to a solution for contact lenses containing no, or only a trace amount of, polylysine. According to this method, an available solution for contact lenses that is not designed to fit the object of the present invention can be made into a solution according to the invention for preservation and/or disinfection.

The thus prepared solution for contact lens preservation and/or disinfection according to the present invention is protected from growth of bacteria and the like in the container, even after the container is opened. In addition, it is useful for convenient disinfection, one of the objects of the present invention.

That is, one of the most effective usages of the solution for contact lenses according to the present invention is the method in which a contact lens after use is immersed in the solution for several hours or overnight and then worn simply after light rinsing with the solution.

It seems to take a considerable time for the antimicrobial component to come into contact with every bacterium and the like adhered to a contact lens, exert its antimicrobial activity, and finish its action. It is also anticipated that the condition of the adhering bacteria and the like, such as the kind and amount thereof, varies among the kinds of lenses. Accordingly, the time of immersing a contact lens in the preserving or disinfecting solution of the invention is not particularly limited as long as disinfection is substantially achieved.

The above-described usage, although of course also applicable to hard contact lenses, is particularly effective in disinfection of water-containing soft contact lenses.

As mentioned in the "Background Art" section, disinfection of water-containing soft contact lenses has been accompanied by various disadvantages to users. All such disadvantages can be eliminated simultaneously by the use of the preserving and disinfecting solution of the present invention since no special equipment is required, a separate solution apart from a solution for preservation is not necessary, and no special care is needed after disinfection.

The solution for contact lens preservation and/or disinfection according to the present invention can contain surface active agents for the purpose of cleaning off lipids lightly adhered on the surface of a contact lens. From the standpoint of low irritation to the eye mucosa, preferred are nonionic surface active agents such as polyoxyethylene glycol alkylphenyl ethers, polyoxyethylene-polyoxypropylene condensates, alkyl polyoxyethylene ethers, polyoxyethylene ethers of glycerides, polyoxyethylene ethers of sorbitan esters, sorbitol polyoxyethylene ethers, and polyethylene glycol fatty acid esters.

Similarly, the solution can contain proteolytic enzymes, such as papain and subtilisin, for the purpose of cleaning off proteins adhered to a lens while worn and lipid decomposing enzymes, such as lipase, for the purpose of cleaning off fatty dirt. Pancreatin can be mentioned as an example of particularly suitable enzymes that can clean off lipids, proteins, and glucide simultaneously.

With regard to the content of these additives, the surface active agents are added at a concentration of 0.1 to 15% by weight, more preferably from 0.5 to 10% by weight, and the enzymes are added at a concentration of from 0.005 to 5% by weight, more preferably from 0.05 to 1% by weight.

EXAMPLES

The present invention will be illustrated in greater detail by way of Examples, but the present invention is not construed as being limited thereto.

In the Examples the antimicrobial effect of the polylysine solutions for contact lens preservation and disinfection was evaluated by the Sterility Test method specified in Japanese Pharmacopeia (J.P.).

That is, the antibacterial effect of the solution for contact lens preservation and disinfection was confirmed as follows. A medium having the following formulation was prepared. A 15 ml portion of the medium prepared was put into a test tube, and 1 ml of a test solution was added thereto. After incubation at 30 to 32° C. for 7 days, the presence or absence of bacteria was observed with the naked eye.

The medium used in the test was separately subjected to a medium performance test as specified in J.P. Formulation of Test Medium used for Culturing of Bacteria:

| | |
|---|---|
| L-Cystine | 0.5 g |
| Agar | 0.8 g |
| Sodium chloride | 2.5 g |
| Glucose | 5.0 g |
| Yeast extract | 5.0 g |
| Casein acid peptone | 15.0 g |
| Sodium thioglycolate | 0.5 g |
| Resazurin solution (1→1000) | 1.0 ml |
| Water | 1000 ml |

For confirming the antifungal effect, a medium having the following formulation was prepared. A 15 ml portion of the medium prepared was put into a test tube, and 1 ml of a test solution was added thereto. After incubation at 20 to 25° C. for 10 days, the presence or absence of fungi was observed with the naked eye.

The medium used in the test was separately subjected to a medium performance test as specified in J.P. Formulation of Test Medium used for Culturing Fungi:

| | |
|---|---|
| Potassium dihydrogenphosphate | 1.0 g |
| Magnesium sulfate | 0.5 g |
| Casein peptone | 5.0 g |
| Yeast extract | 2.0 g |
| Glucose | 20.0 g |
| Water | 1000 ml |

Example 1

A solution for contact lens preservation and disinfection was prepared according to the following formulation. Poly-L-lysine available from Sigma Co. was used as polylysine.

| | |
|---|---|
| Sterile purified water | 98.72 wt % |
| Sodium chloride | 0.5 wt % |
| Potassium chloride | 0.1 wt % |
| Boric acid | 0.5 wt % |
| Borax | 0.05 wt % |
| EDTA-2Na | 0.09 wt % |
| Polylysine | 0.04 wt % |

A vial having a capacity of about 5 ml was filled with the solution. A water-containing soft contact lens (Aime Soft S, produced by Asahi Chemical Aime K.K.) after being worn all day, was, without being cleansed, put in the vial. After 14 days, the solution in the vial was sampled, and the presence or absence of any bacteria or fungus was examined according to the Sterility Test method described in J.P. As a result, no change was observed with the culture medium.

Then, the medium used for the Sterility Test on bacteria was sampled and made into a smear preparation and Gram stained. More specifically, the medium was smeared and fixed on a slide glass and stained for 1 minute with a basic dye, Crystal Violet, mordanted with a Lugol's iodine solution for 1 minute, and immersed in 95% ethanol for 30 seconds. Microscopic examination of the stained smear revealed no existence of bacteria.

As for fungi, a platinum loopful of the culture medium was transferred to a fresh medium of the same composition. After incubation at 20 to 25° C. for 10 days, the presence or absence of any fungi was confirmed with the naked eye, but no existence was recognized.

From the foregoing the solution in the vial was proved germ-free.

In order to confirm that polylysine in the solution had not penetrated into the lens material, the lens was left to stand in a vacuum desiccator at 25° C. for 16 hours to dry completely, broken into fine pieces, and made into a tablet by a KBr tablet method (the pieces of the lens were mixed with KBr powder and press molded into a disc). The IR absorption spectrum measured with an IR absorption spectrometer (FT/IR-300E, manufactured by Nippon Bunko K.K.) showed no peak assigned to an amido group (1550 and 1650 $cm^{-1}$).

Comparative Example 1

The same procedure as in Example 1 was repeated, except that a solution prepared according to the following formulation was used and that the IR absorption analysis was omitted. As a result, white turbidity was clearly perceived to the naked eye in the medium for bacteria culturing, indicating growth of bacteria.

Growth of fungi was also found with the naked eye in the medium for fungi culturing.

| Sterile purified water | 98.76 wt % |
| Sodium chloride | 0.5 wt % |
| Potassium chloride | 0.1 wt % |
| Boric acid | 0.5 wt % |
| Borax | 0.05 wt % |
| EDTA-2Na | 0.09 wt % |

Example 2

The same procedure as in Example 1 was repeated, except that a high-silicone hard contact lens (Aime $O_2$, produced by Asahi Chemical Aime K.K.) was preserved in an aqueous solution prepared according to the following formulation, and the IR absorption analysis was omitted. As a result, the solution was proved germ-free.

| Sterile purified water | 94.76 wt % |
| Sodium chloride | 0.5 wt % |
| Potassium chloride | 0.1 wt % |
| Boric acid | 0.5 wt % |
| Borax | 0.05 wt % |
| EDTA-2Na | 0.09 wt % |
| Ethanol preparation of polylysine* | 4.0 wt % |

*The ethanol preparation of polylysine used in Example 2 comprises an approximately 68% aqueous solution of ethanol having dissolved therein polylysine in a concentration of 0.3% (Guard Power UP 733C, produced by Chisso Corp.).

Example 3

The same procedure as in Example 1 was repeated except for using a solution prepared according to the following formulation and omitting the IR absorption analysis. As a result, the solution was proved germ-free.

| Sterile purified water | 99.05 wt % |
| Sodium chloride | 0.9 wt % |
| Polylysine (the same as used in Example 1) | 0.05 wt % |

Example 4

In this Example the effect of polylysine formulated into granules was demonstrated.

The components shown in the following formulation were mixed by agitation in a porcelain mortar. Ten grams of a 10% aqueous solution of polylysine was added thereto, followed by kneading. The polylysine used here was the same as that used in Example 1.

| Sodium chloride | 39.1 g |
| Potassium chloride | 7.8 g |
| Boric acid | 39.1 g |
| Borax | 3.9 g |
| EDTA-2Na | 7.0 g |

The resulting semi-pasty mixture was forced through a sieve having 850×850 μm openings with a rubber spatula and dried in a constant temperature drier (FS-320, Advantec Toyo K.K.) set at 60° C. for 16 hours, followed by cooling to room temperature to obtain granules.

A 1.28 g portion weighed out of the granules was dissolved in 100 ml of water to prepare a solution for preservation and disinfection.

The same procedure as in Example 1 was repeated except for using the solution prepared and omitting the IR absorption analysis. As a result, the solution showed quite the same effects as observed with the solution of Example 1.

Reference Example

A solution prepared according to the following formulation was inoculated with a microbial cell suspension and incubated at 25° C. After 7 day's and 14 day's incubation, the number of vital cells per ml was counted. The cell suspension was prepared by cultivating the bacterium shown below on a broth agar slant medium at 35° C. for 18 to 24 hours and suspending the microbial cells in sterilized physiological saline. Enumeration of bacteria was carried out in accordance with the Pour Plate Culture Method using an SCDLP (produced by Nihon Seiyaku K.K.) agar medium.

| Sterile purified water | 98.757 wt % |
| Sodium chloride | 0.5 wt % |
| Potassium chloride | 0.1 wt % |
| Boric acid | 0.5 wt % |
| Borax | 0.05 wt % |
| EDTA-2Na | 0.09 wt % |
| Polylysine | 0.003 wt % |

For comparison, the same test was repeated except for excluding polylysine from the above formulation. The decrease was offset by an increase of sterile purified water (i.e., the proportion of the sterile purified water was changed to 98.76 wt %). The results obtained are shown below.

The results of the above test (Microbial Limits Test) were as follows.

| Test Bacterium | Number of Added Cells | Days of Preservation 7 | 14 |
|---|---|---|---|
| Polylysine Added | | | |
| Escherichia coli | $1.7 \times 10^6$ | undetected | undetected |
| Pseudomonas aeruginosa | $2.3 \times 10^6$ | " | " |
| Staphylococcus aureaus | $1.5 \times 10^6$ | " | " |
| Polylysine not Added | | | |
| Escherichia coli | $2.5 \times 10^6$ | $5.3 \times 10^6$ | $9.1 \times 10^5$ |
| Pseudomonas aeruginosa | $9.5 \times 10^6$ | $3.3 \times 10^5$ | $2.4 \times 10^6$ |
| Staphylococcus aureaus | $1.3 \times 10^6$ | 16 | undetected |

Industrial Applicability

The solution for contact lens preservation and/or disinfection according to the present invention is an aqueous solution suitable for preservation of contact lenses. Containing polylysine, it is applicable to any kind of contact lenses. It is used for both preservation and disinfection, making the handling of contact lenses easier and simpler.

The solution is of high safety because the polylysine of the solution scarcely penetrates or accumulates in the inside of a contact lens while the solution is used for the preservation and/or disinfection.

Further, the solution of the invention can be used with safety, guaranteed against reduction in quality during long-term storage after its preparation. The solution can be used as such during high-temperature sterilization by autoclaving.

What is claimed is:

1. A solution for preserving a contact lens comprising ε-polylysine.

2. The solution according to claim 1, wherein the content of said ε-polylysine is in the range of from 1 ppm to 10%.

3. The solution according to claim 2, wherein said ε-polylysine content is in the range of from 10 ppm to 1%.

4. A solution for disinfecting a contact lens comprising ε-polylysine.

5. A solution for preserving and disinfecting a contact lens comprising ε-polylysine.

6. A method for either or both of preserving and disinfecting a contact lens comprising using a solution containing ε-polylysine.

7. An aqueous solution for storing and disinfecting contact lenses, comprising a majority of water and from about 1 ppm to about 10% by weight ε-polylysine.

8. The solution according to claim 7, containing from about 10 ppm to about 1% by weight ε-polylysine.

9. The solution according to claim 7, for storing contact lenses, containing from about 10 ppm to about 1000 ppm ε-polylysine.

10. The solution according to claim 7, for disinfecting contact lenses, containing from about 100 ppm to about 1% by weight ε-polylysine.

11. A solution for storing and disinfecting contact lenses, comprising from about 1 ppm to about 10% by weight ε-polylysine, in a dilute aqueous solution further comprising an inorganic acid salt selected from the group consisting of sodium chloride, potassium chloride and magnesium chloride in an amount of up to about 3% by weight.

* * * * *